(12) United States Patent
Ismail

(10) Patent No.: US 11,648,332 B1
(45) Date of Patent: May 16, 2023

(54) UNIVERSAL AIR PURIFICATION SYSTEM

(71) Applicant: Innovative Technologies, Waltham, MA (US)

(72) Inventor: Nassar Ismail, Dover, MA (US)

(73) Assignee: Innovative Technologies, Waltham, MA (US)

( * ) Notice: Subject to any disclaimer, the term of this patent is extended or adjusted under 35 U.S.C. 154(b) by 0 days.

(21) Appl. No.: 17/727,266

(22) Filed: Apr. 22, 2022

(51) Int. Cl.
*A61L 9/20* (2006.01)
*F24F 8/22* (2021.01)
*F24F 8/158* (2021.01)
*F24F 8/108* (2021.01)
*G05D 1/02* (2020.01)
*F24F 6/00* (2006.01)
*F24F 110/50* (2018.01)

(52) U.S. Cl.
CPC ............... *A61L 9/20* (2013.01); *F24F 8/108* (2021.01); *F24F 8/158* (2021.01); *F24F 8/22* (2021.01); *G05D 1/0212* (2013.01); *A61L 2209/111* (2013.01); *A61L 2209/14* (2013.01); *F24F 2006/008* (2013.01); *F24F 2110/50* (2018.01)

(58) Field of Classification Search
CPC .. A61L 9/20; A61L 2209/111; A61L 2209/14; F24F 8/22; F24F 8/158; F24F 2006/008; F24F 2110/50; B01D 50/00; B01D 39/00
USPC ........ 55/418, DIG. 34; 96/224; 422/24, 121, 422/122, 124, 169, 171, 172; 250/432 R
See application file for complete search history.

(56) References Cited

U.S. PATENT DOCUMENTS

| | | | |
|---|---|---|---|
| 6,022,511 A | 2/2000 | Matschke | |
| 6,221,314 B1* | 4/2001 | Bigelow | A62B 29/00 422/186 |
| 6,383,244 B1* | 5/2002 | Wake | B01D 29/58 55/482 |
| 6,500,387 B1* | 12/2002 | Bigelow | A61L 9/20 55/286 |
| 6,666,912 B1* | 12/2003 | Yan | A61L 9/20 55/472 |
| 6,849,107 B1 | 2/2005 | Huffman | |
| 6,939,397 B2* | 9/2005 | Nelsen | B03C 3/32 422/124 |
| 6,984,259 B2 | 1/2006 | Hurst | |
| 7,247,237 B2* | 7/2007 | Mori | B01D 39/1692 422/177 |
| 7,421,851 B2 | 9/2008 | Witham | |
| 7,597,856 B2 | 10/2009 | Naarup | |
| 8,252,100 B2 | 8/2012 | Worrilow | |
| 9,821,260 B2* | 11/2017 | Stoner, Jr. | B01D 46/62 |
| 10,632,411 B2* | 4/2020 | Williams | B01D 39/083 |
| 2003/0131734 A1 | 7/2003 | Engel | |

(Continued)

FOREIGN PATENT DOCUMENTS

RU 2 610 923 C1 2/2017
WO 2007070704 A2 6/2007

*Primary Examiner* — Minh Chau T Pham
(74) *Attorney, Agent, or Firm* — Lambert Shortell & Connaughton; David J. Connaughton, Jr.; Justin P. Tinger

(57) ABSTRACT

An air purification system is provided. The air purification system utilizes a multi-pronged approach to both filter air as well as irradiate it with ultraviolet light. Optionally, a humidifier and/or dehumidifier may be used to further treat the outlet air. The system may be positioned fixedly in building air ducts, or may be used in mobile applications to treat and purify air in a room or other space.

23 Claims, 8 Drawing Sheets

(56) References Cited

U.S. PATENT DOCUMENTS

| | | | |
|---|---|---|---|
| 2005/0183576 A1* | 8/2005 | Taylor | B03C 3/365 96/60 |
| 2005/0190568 A1 | 9/2005 | Sevack | |
| 2006/0057020 A1 | 3/2006 | Tufo | |
| 2006/0201119 A1* | 9/2006 | Song | B01D 53/007 55/471 |
| 2006/0215257 A1 | 9/2006 | Morrow | |
| 2008/0112845 A1 | 5/2008 | Dunn | |

* cited by examiner

UNIVERSAL AIR PURIFICATION SYSTEM

BACKGROUND

Technical Field

The present disclosure relates generally to air filtering systems. More particularly the present disclosure relates to an air purification system which filters and treats the filtered air with ultraviolet (UV) to further damage or destroy pathogens.

Description of Related Art

The SARS-Cov-2 (COVID-19) pandemic has exposed the dire need for a clean, healthy environment. In particular, enclosed environments, including schools, hospitals, airplanes, restaurants, office buildings, stores, and the like are in desperate need for clean air to prevent the spread of airborne and droplet-borne disease.

Further, as climate change progresses, the incidence of severe weather events such as hurricanes, flooding, and other storms increases. This in turn leads to an increase in mold and fungus in living spaces such as on and in walls and ceilings. Excess mold and fungus spores in the air can lead to a number of negative health outcomes.

Current solutions to protect from such pathogens, including COVID-19, is to wear a face mask, keep distance from people, wash hands and the like. Vaccines and in some cases medications also are of some help. All of these solutions, however require some level of inconvenience and challenge to people, including refusal of many to wear a mask, get vaccinated, and take proper precautions when sick.

Current air filtration and purification systems are inefficient and in many cases result in too high a pressure drop across the filter to be applied in many existing duct systems. Too high a pressure drop results in strain and leakage in existing systems as well as reduced air flow and reduced heating/cooling efficiency due to increased pressure on the upstream side of the filter. Essentially, the existing filters reduce the flow through the duct too much to be practical and can cause other problems. Further still, existing systems are hard to upscale and are generally limited to specific uses rather than broad ranging systems applicable in many environments.

Therefore, what is needed is a highly efficient air purification system that can use filtration combined with UV light treatment to provide a highly pure, humidity balanced air output.

SUMMARY

The subject matter of this application may involve, in some cases, interrelated products, alternative solutions to a particular problem, and/or a plurality of different uses of a single system or article.

In one aspect, an air purification system is provided. The air purification system has a filter formed into a cylinder, conical frustum shape, or other curved shape such that the curved surface provides an increased filtering surface area compared to a flat filter arranged perpendicular to air flow. The filter may further define an interior space. The filter may be formed of a filter material which is thicker at a first end than at a second end. This allows the filter to efficiently filter accommodating for the pressure drop along the length of the filter. At areas along the filter having higher pressure, the thicker filter is used, and at areas having lower pressure, a thinner filter may be used. Within the interior space of the filter is an ultraviolet lamp or other UV light source operable to irradiate air after it has passed through the filter. This UV irradiation provides further purification by killing, damaging, or breaking down pathogens and other biological material. The ultraviolet lamp is at least partially surrounded by a reflector positioned within the interior space, the reflector is operable to reflect ultraviolet light from the ultraviolet lamp, and positioned to prevent exposure of the filter to the ultraviolet light from the ultraviolet lamp.

In another aspect, the air purification system may further include a conveyance system allowing it to move within a room, building, space, and the like where air purification is desired. In addition to the features noted above, this aspect may include the conveyance system having one or a plurality of wheels, a motor operable to move the one or plurality of wheels, and a computer controller which allows for controlled movement of the air purification system. Such a system may also include a fan or similar blower which conveys air through the air purification system. A motor operating the fan or blower may be, in one embodiment, a universal motor which can run on any one of an AC or DC power supply, or both.

In certain embodiments, a computer controller may be in communication with components of the air purification system such as a fan, the UV light source, conveyance systems, and the like. This computer controller may have a wireless or wired connection that allows a user to control operation of the system. The computer controller may have a wireless receiver or transceiver in some embodiments such as a Bluetooth®, WiFi, cellular or other wireless communication system. As such, a user may access control of the system using a remote computerized user interface to control aspects of system operation.

In yet another aspect, the air purification system noted above is positioned in an air duct. The air purification system operates to filter and treat air entering and within the duct as it passes through. The air purification system is connected to the air duct via a seal which forces air flow around the filter and causes air to pass through the filter to the duct as cleaner air, as seen in, for example, FIG. 1.

In yet another aspect, a method of air purification is provided. The method involves an air purification system in an air duct. Air passes through the air duct and through a filter of the air purification system. The filter is formed of a filter material, wherein the filter material has a first thickness at a first end of the filter and second thickness at a second end of the filter, the first thickness being greater than the second thickness and, in this aspect, has a tapering thickness from one end to the other. Of course, depending on filter configuration, many different thicknesses may be present along the length of the filter. After filtration the air is exposed to ultraviolet light from an ultraviolet light source. This ultraviolet light source positioned within an interior space defined by the filter, and includes a reflector positioned within the interior space between the ultraviolet light source and the filter to prevent degradation of the filter material by ultraviolet light and to reflect the UV light back to the pathogen killing area instead of it being absorbed by the filtration material instead. The filtered and ultraviolet-exposed air then passes out of the air purification system through an outlet.

DETAILED DESCRIPTION

Figure 1:
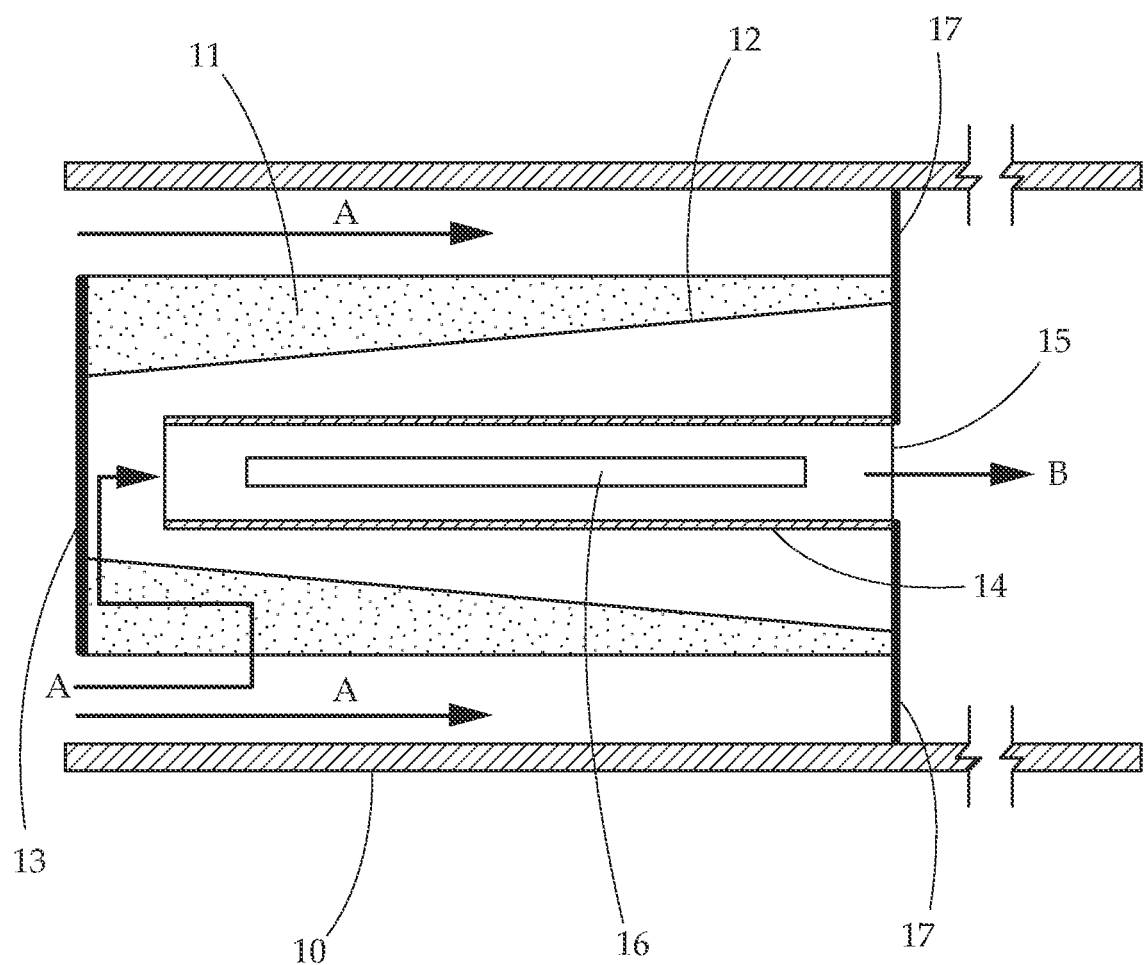
FIG. 1 provides a side view of an embodiment of the air purification system positioned in an air duct.

The detailed description set forth below in connection with the appended drawings is intended as a description of presently preferred embodiments of the invention and does not represent the only forms in which the present disclosure may be constructed and/or utilized. The description sets forth the functions and the sequence of steps for constructing and operating the invention in connection with the illustrated embodiments.

Generally, the present disclosure concerns an air purification system for use in treatment of air in indoor or other enclosed spaces. As noted, purification of air to remove pathogens, including germs, fungus, mold, droplets, aerosols, particulate matter, and the like is become increasingly critical since the COVID-19 pandemic as well as an increase in storms including hurricanes, and floods. This trend will only continue further as the importance of limiting the spread of disease and infection continues to be appreciated. The air purification system of the present disclosure operates on two or more stage system. The first stage is a filtration of the air to remove particles, droplets, aerosols, and the like which may contain pathogens. In some embodiments, the filtration stage(s) also removes germs including bacteria and/or viruses (included but not limited to coronaviruses) from the air. The second stage involves irradiating the filtered air with ultraviolet ("UV") light to further kill, damage, deactivate or otherwise breakdown bacteria, molds, funguses, viruses, spores, and any other biological material that may have escaped previous filter(s). In some further embodiments, a humidifier and/or dehumidifier may be used to further treat the air to provide the output air at a desirable humidity level.

Importantly, the filter of the air purification is curved to create a greater surface area for filtration. Also, the thickness of the filter material is tapering such that an area of the filter exposed to higher pressure has a thicker filter wall, while a lower pressure area has a thinner filter. For example, in embodiments having a higher pressure on an upstream part of the filter, with pressure gradually decreasing along the length of the filter, the filter material is thicker upstream and tapers to a thinner downstream filter. In configurations having a higher pressure downstream (due to, for example, filter causing a backup in air flow), the downstream side may be thicker than the upstream side. This configuration may also be appropriate where the upstream side of a filter has a faster airflow over it and thus a lower pressure than a downstream side.

The filter may be formed of any material capable of filtering air flowing through it. Preferably, the filter is capable of trapping at least droplets and dust particles, and in many cases is able to also filter out finer particulates such as aerosols and virus particles. The filter may be a single layer or may be comprised of a plurality of layers. At least one of the layers, in a multi-layered embodiment is configured to have a tapering thickness such that one end is thicker than an opposite end. Sizing of the filter is based on intended operation, including flow rate and operating pressure. In one embodiment, the filter thickness variation may be selected to provide an approximately equal flow rate through the filter at the thick end and thin end, such that flow through the filter is very efficient and uniform. In another embodiment, the filter thickness variation may be selected to provide an approximately equal internal pressure such that air passing through the thicker end of the filter enters the interior space of the filter at approximately the same pressure as air passing through the thinner end of the filter. In other words this embodiment has a varying pressure drop across the filter, and is sized based on expected operating parameters to have the pressure drop result in a uniform internal pressure on the inner side of the filter.

In yet another embodiment, the filter may be configured to have an approximately uniform volume flow rate per unit area along its length. In such an embodiment, operational pressure may be modeled and then the thickness (and corresponding flow-resistance) may be determined such that volume flow will be approximately equal, with higher pressure areas having a thicker filter and lower or different pressure areas having a thinner filter area to allow air to flow through at an approximately even volume flow at both high and low pressure areas. Of course, other configurations of the filter may be selected depending on goals of the air purification system, so long as the filter is thicker at a higher inlet pressure area and thinner at a lower inlet pressure area. As discussed further in the figures, in some embodiments, the filter may be pleated, and in other embodiments not pleated. Most embodiments of the filter are formed as a cylinder or conical frustrum, though of course shape may vary within the scope of this disclosure.

Many existing air purification systems can not be used for HVAC systems, especially existing HVAC systems which are generally only configured for minor filtration at an inlet register. However, the present disclosure can be as long as the duct system requires to limit pressure drop across the filter to accommodate for a particular system's requirements. The cylindrical or conical frustum shape can be easily adapted to a longer duct pipe to supply the desired air volume to a particular system. The system may be scaled for home or office use, hospital use, cruise ship or airplane use, and the like.

In a particular embodiment of a multi-layered filter, the multiple layers may include various combinations of: A coarse filter layer or layers which may be any well-known air filter material to trap larger components, a high efficiency particulate air ("HEPA) filter layer or layers, and/or a charcoal filter layer or layers. In the multi-layered embodiments, at least one layer of the multiple layers has a tapering thickness, and more than one layer may have tapering thicknesses.

The UV treatment stage may be formed of a UV lamp or lamps, or similar UV light source(s), coupled with a reflector. The reflector or reflectors may serve two purposes. The first is that it reflects the UV light across the air flow path repeatedly which in some cases saves up to 70% of the UV light, rather than having the UV light be absorbed by the absorbent filter material. The second is that it prevents UV light from substantially contacting the filter material, which will damage and break down the filter material over time causing a short lifespan of the filter. The UV reflector may be formed of any material capable of substantially reflecting UV light, typically metal and most typically aluminum. The reflector is configured to allow entry of the filtered air to direct it past the UV light source and then to an outlet to expel the filtered and irradiated air. In some embodiments, this flow path may be formed partially or totally by a reflective material, and in other embodiments, only part of the material preventing UV light from reaching the filter may be reflective. It is known that most UV light—specifically UV-germicidal ("UV-G") light is absorbed by surrounding materials. In fact, paint and white wallpaper absorbs approximately 94% of UV-G light. Accordingly, the reflector substantially decreases absorption on adjacent surfaces, instead reflecting the germicidal light back at the air stream, increasing the UV treatment efficiency in the air stream.

In some embodiments, the air purification system may be battery powered and mounted on a conveyance system to allow it to be portable and move from room to room and to different areas in a room or space. In one embodiment, movement may be automated in a similar manner to automated vacuum cleaners. Movement may be pre-programmed within the room and informed by sensors to inform the conveyance system when it is approaching an object. In a particular embodiment, air quality sensors such as particulate sensors, humidity sensor, Co2 sensor, pathogen sensor and the like may be used to cause the air purification to linger longer in an area having an indicator of poor air quality. A fan or other tool to cause air flow through the filter is positioned on the mobile version. In certain embodiments air inlet may be from a bottom of the portable air purification system, however due to the configuration of the filter and its tapering walls, air may enter and be filtered all along the length due to the more narrow filter material away from the air inlet. In the prior art, air enters only at the bottom of a cylindrical filter, while the present disclosure allows entrance of air along the entire length of the filter, greatly increasing the surface area through which air may pass. This allows for a much larger surface area of filter to be used compared to the prior art.

A humidifier and/or dehumidifier may be positioned downstream of the air flow from the filter. This provides an outlet air flow with the proper and comfortable amount of moisture. Many humidifiers in the prior art use regular water from a tap or other general water source. This water and corresponding piping generates mold and pathogens, which are introduced into the air by the humidifier and cause illness or allergy to system users. To remedy this and maintain a purified air stream, the humidifier contemplated herein may in some embodiments use a purified water and may comprise a water purification system including but not limited to a filter, membrane, chemical treatment, and/or radiation treatment.

In many embodiments, the filter may also operate to diminish the effect of nuclear alpha and beta radiations caused by, for example, nuclear fallout. This diminishing of alpha and beta radiations may be achieved by forcing the airflow to follow a longer path and changing direction. This forces the radiation in the air to hit the obstructing targets, leaving the air filtered and cleared of radiation. In other words, the blockage of air flow system will force this type of nuclear radiation to "hit" the obstructing walls such as the filter and reflectors, cleaning the air. As is known in the art, while inhaling alpha particles cause severe health hazards, a thin sheet of paper (or reflector material), will be sufficient to mitigate this problem. In a particular embodiment, the air purification system components (including filter, metal filter frame, and reflector) may be electrically grounded by electrically connecting to a ground of a power source operating the air flow and/or UV source of the air purification system. By grounding the components, charged particle radiation can be received on these components and discharged to ground.

In a particular embodiment, a shut-off switch is easily accessible on or near the air purification system. The shut off switch is important to deactivate the UV light source so that it does not expose an operator to excess damaging radiation. In some such embodiments, the shut-off switch may be automatic such that if the duct is opened, filter is moved/removed, or other disruption of operating configuration, the automatic shut-off switch may be triggered, preventing operation of the UV light source. This can improve safety of the device to operators, installers, maintenance workers, and end users.

In one embodiment, the air purification system may include a battery backup which allows air to flow through the system in the event of a power loss. The battery backup is operable to power a fan or blower to convey air through the air purification system, and operable to power the UV light source as well. Power outages occur during storms, and other catastrophe or disaster situations. These are just the type of situations where operation of the air purification system is most needed. For example, during a storm there may be flooding which can substantially negatively impact air quality. The battery backup allows the air purification to continue to operate in a flooding situation. Similarly, in the case of a biological or nuclear weapon attack, the system may be operable to purify the air and keep occupants safe. Furthermore, the battery will allow the system to move around freely without being attached to a wall (through power cord).

Turning now to FIG. 1, a side cutaway view of an embodiment of the air purification system is provided. The air purification system is positioned in a duct 10 allowing airflow A to pass through which exits the air purification system as purified flow B through outlet 15. The air purification system 11 has a filter 12 which has a thickness which tapers from a thick end to a thinner end. This thickness taper corresponds to regions within the duct 11 having higher or lower pressures. In this view, at the upstream end, filter 12 is thicker than at the downstream end because, in this configuration, there is more air upstream and as it gets drawn into and through the filter, there is less air to pass through at the downstream end. A thinner filter at the downstream end allows adequate air flow through the filter, thereby increasing the overall area of the filter which can be used for filtration, and therefore allowing a greater air flow through the filter. The air purification system 11 is sealed to the duct at seals 17 to prevent air from passing over and around the filter, ensuring that all of air flow A goes through the filter 12. As will be understood, filter thickness taper may not be so drastic, and this is shown for display purposes. Depending on embodiment, tapering or other thickness reductions may be much more subtle. Other configurations to cause thickness of the filter to be thicker on one and thinner at another may be used.

In some embodiments, a step down in filter thickness may be used rather than a gradual taper. In one embodiment, a second, third, or more layers of a filter material may be used to increase the thickness in a stepwise manner. For example, at the thickest first end of the filter, three layers of a filter material may be used. Partway along the length of the filter, only two layers may be used, and towards a thinnest second end, only one layer may be used. Of course, any number or variation of filter layers may be used in this embodiment without straying from the scope of this invention. Such a configuration may simplify the fabrication process by using a uniform material with various layers as needed. It is to be noted that in this and many other embodiments, the leading front upstream end 13 does not allow entry of air from the front, air-stream A facing surface. Within the filter 12 is an interior space. Within the interior space, air is caused to flow through a space between the reflector 14 and UV lightou source 16 which forms a channel and connects to outlet 15. Enclosed by the reflector is a UV light source 16 which emits UV-germicidal wavelengths to damage, destroy, deactivate and weaken pathogens and other biological materials. As noted above, the reflector 14 functions to both protect the filter material 12 from the UV light which will damage and degrade the material over time, and also serves to increase UV radiation effectiveness and exposure of the air passing through the reflector-defined channel. The reflector 14, in this embodiment, is positioned such that it extends past the ends of the UV source 16. This helps limit exposure of filter 12 to the UV light but preventing escape of nearly all of the UV light from UV source 16 and also improves safety to prevent escape of UV light which may be damaging to humans, animals, and the surrounding materials.

Figure 2:
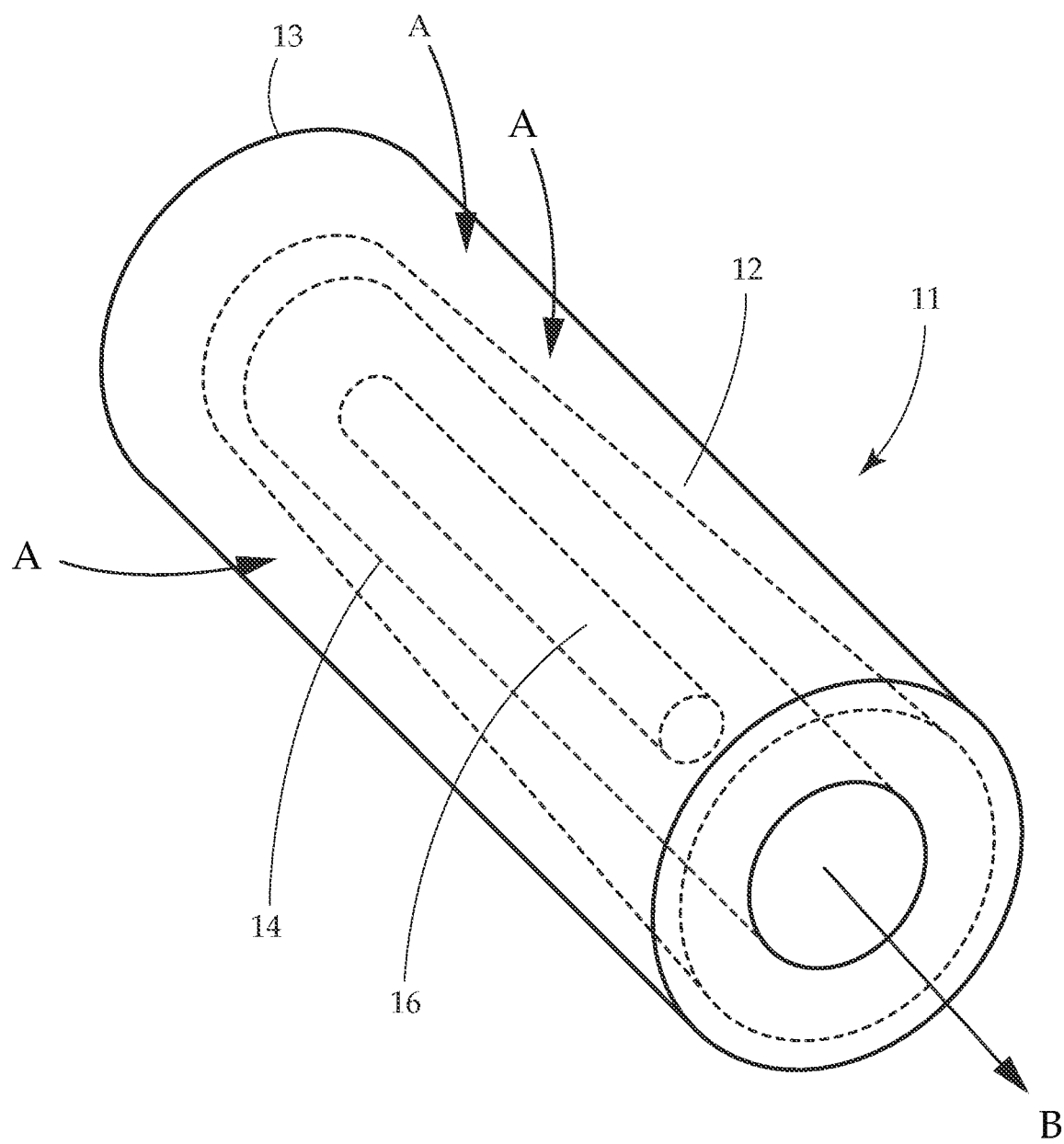
FIG. 2 provides a perspective view of another embodiment of the filtration system of the air purification system.

FIG. 2 shows a perspective view of an embodiment of the air purification system. In this view, the exterior of the filter 12 is cylindrical or approximately so. Filter 12 has a larger thickness at the first end 13 and thinner at the opposite end by outlet 15. Untreated air A enters through the filter, passes through the channel formed by reflector 14 and is exposed to germicidal UV light from UV source 16. The air flow then exits as purified air flow B. The air may then pass to a humidifier/dehumidifier before leaving the system.

Figure 3:
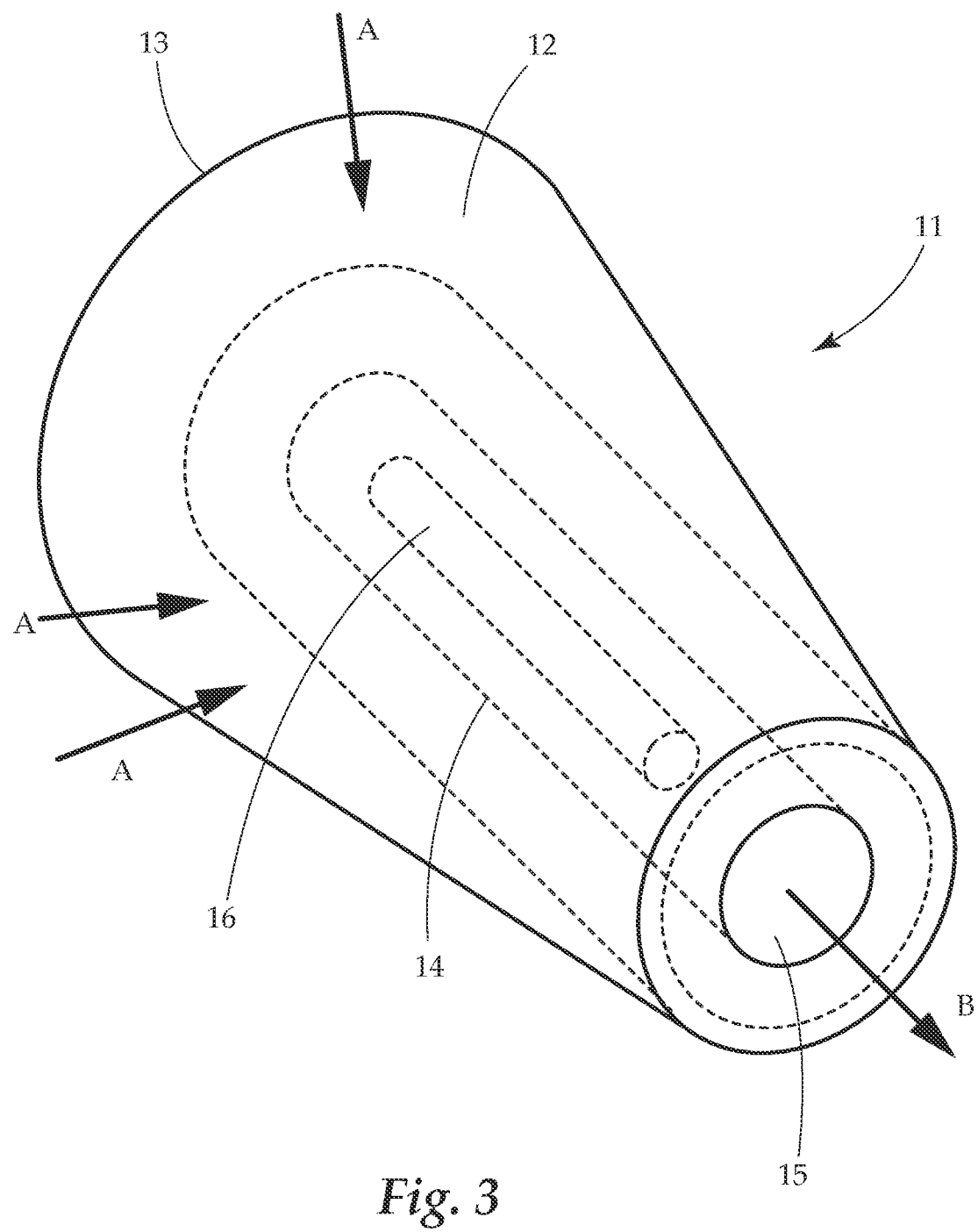
FIG. 3 provides a side view of yet another embodiment of the filtration system of the air purification system.
Figure 4:
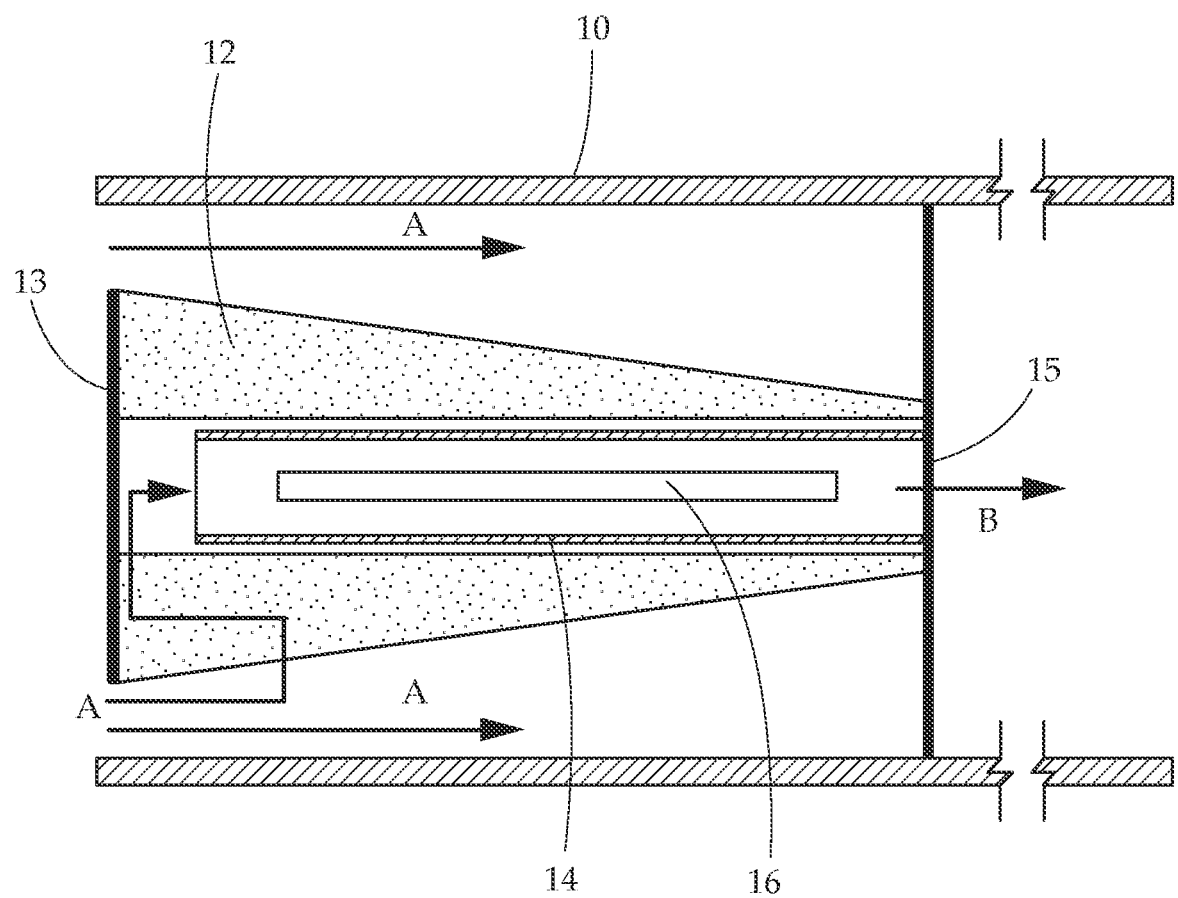
FIG. 4 provides a side view of still another embodiment of the air purification system positioned in an air duct.

FIG. 3 shows a perspective view of an embodiment of the air purification system. In this view, the exterior of the filter 12 is a conical frustum or approximately so. Filter 12 has a larger thickness at the first end 13 and thinner at the opposite end by outlet 15. In this embodiment, the interior space defined by the filter is cylindrical or approximately cylindrical, and filter thickness variation results in the conical frustum shape. As noted above, in some embodiments the tapering may be a steady angled shape, while in other embodiments the tapering may be a progressive step down in thickness caused by cut outs and/or adding/removing layers of material along the length of the filter 12. A cross sectional view of this embodiment can be seen in place in a duct 10 in FIG. 4. The elements of FIG. 4 are similar to that of FIG. 1, with a difference being that the exterior of the filter 12 is shaped as a conical frustum rather than a cylinder as in FIG. 1, and the embodiment of FIG. 4 having a cylindrical interior space containing the reflector 14 and UV source 16.

Figure 5:
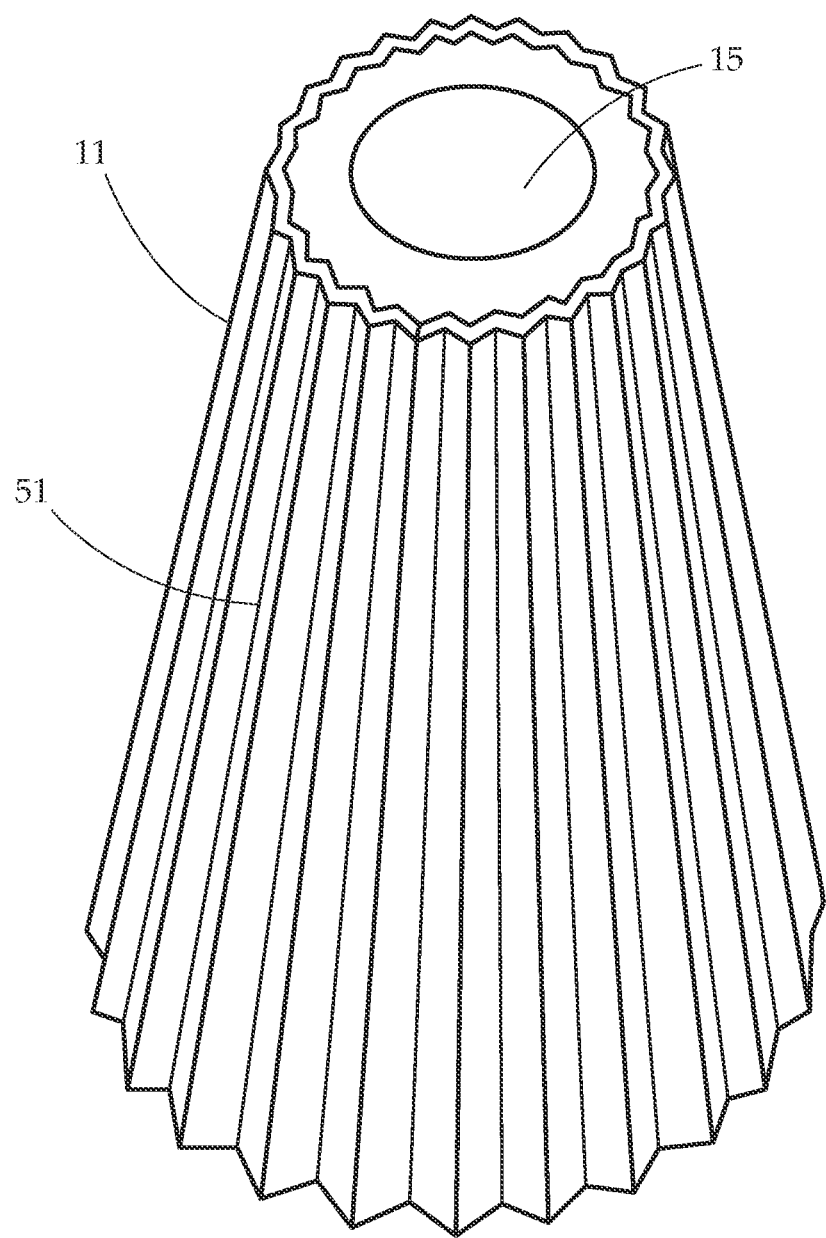
FIG. 5 provides a perspective view of an embodiment of the filtration system.
Figure 6:
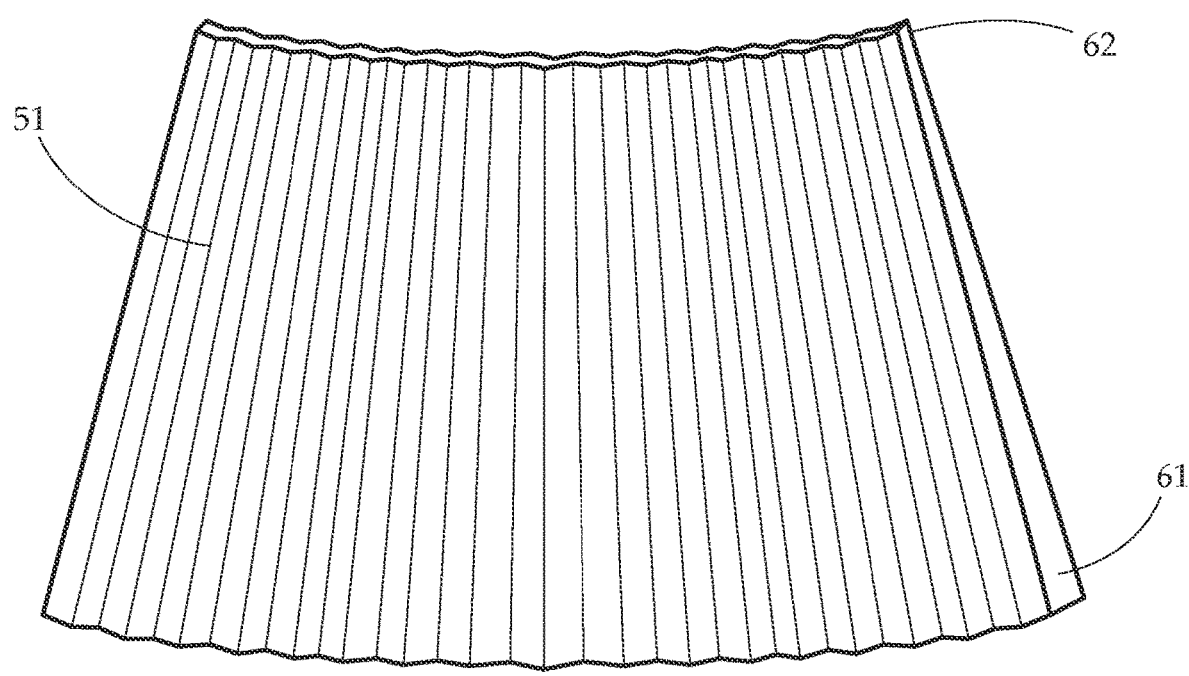
FIG. 6 provides a view of an embodiment of a filter of the system.
Figure 7:
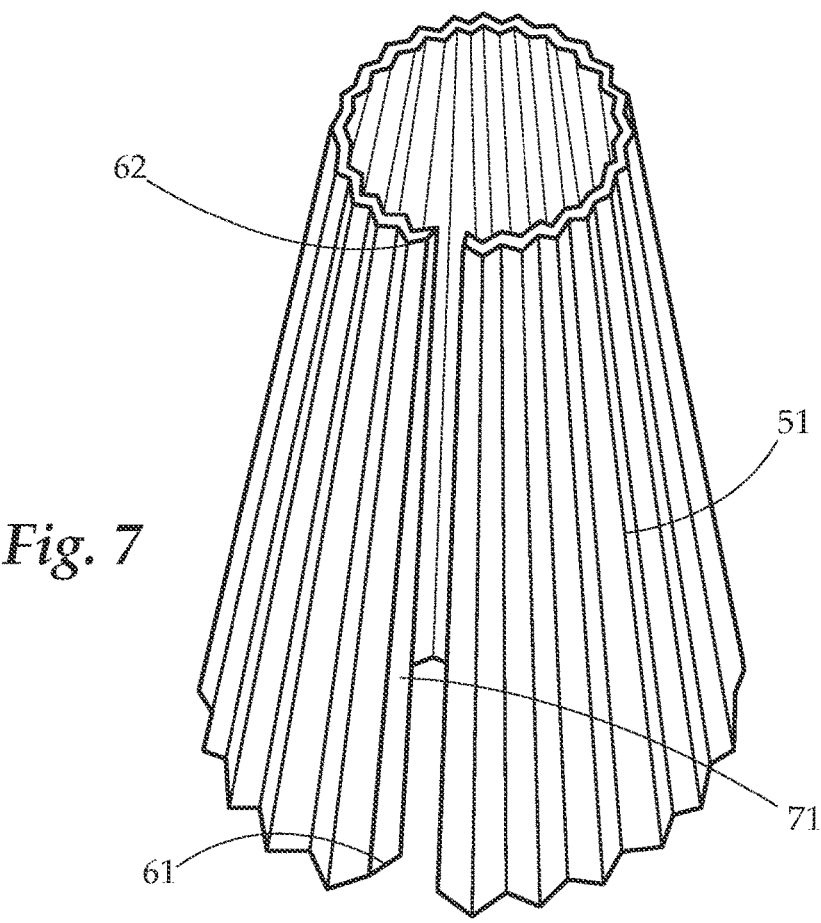
FIG. 7 provides another view of an embodiment of filter of the system

FIGS. 5-7 provide views of an embodiment of the air purification system having pleated filters. In FIGS. 5 and 7, the filter 12 is rounded and shaped as a conical frustum, such that the filter thickness is greater at the bottom than at the top. The filter 12 has pleats 51 which further increase the surface area of the filter allowing greater air flow through the filter by having a greater surface area through which the air may flow. FIG. 6 shows a rectangular quantity of filter having a greater first thickness 61 and thinner second thickness 62. The two ends of the rectangular material may be connected together, forming either a cylindrical or conical frustum shape, and forming the interior space. An example of this can be seen in FIG. 7 where the two ends are nearly connected. When joined at connection area 71, the filter will be capable of operation. Pleats allow adjustment of shape by pulling or squeezing the pleat faces further or closer together, like an accordion.

Figure 8:
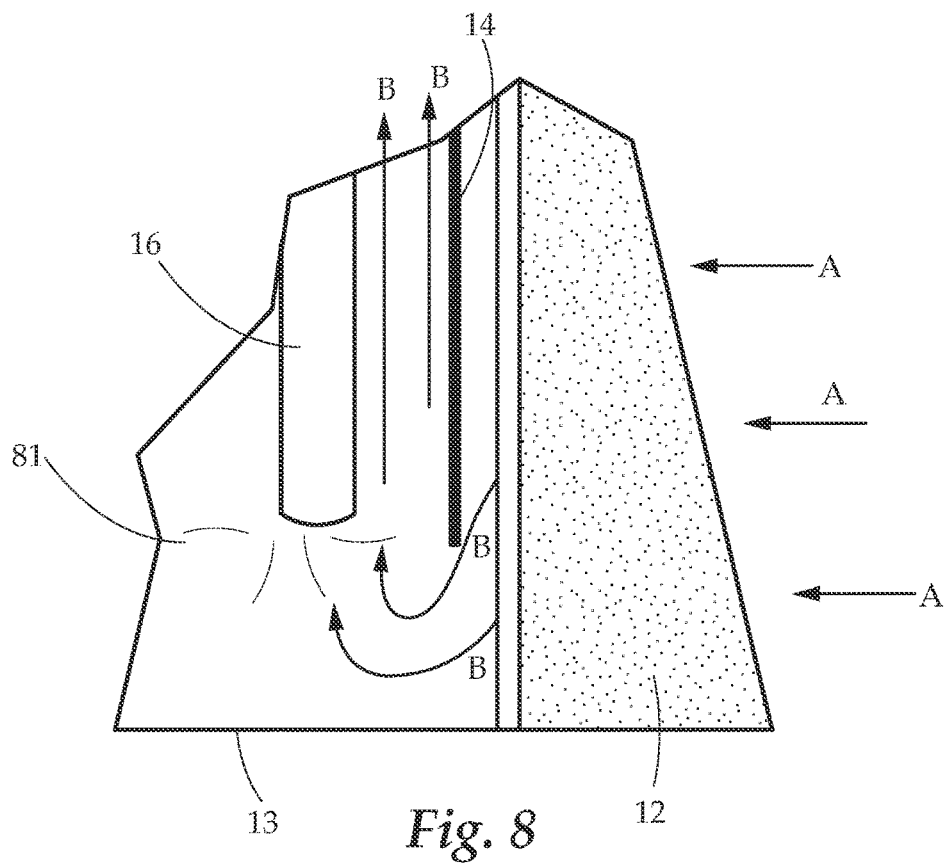
FIG. 8 provides a side detail view of an embodiment of the air purification system.

FIG. 8 provides a detail view of a portion of the air purification system. The tapering filter 12 can be seen thicker at the bottom than at the top. Air A flows into the filter and to the interior space. The reflector 14 defines the channel for the air to flow into and it is then irradiated from UV light 81 from the UV light source 16. As shown in this view, reflector 14 extends beyond the end of the UV light source 16 to limit exposure of the filter 12 to UV light 81 from the UV light source 16.

Figure 9:
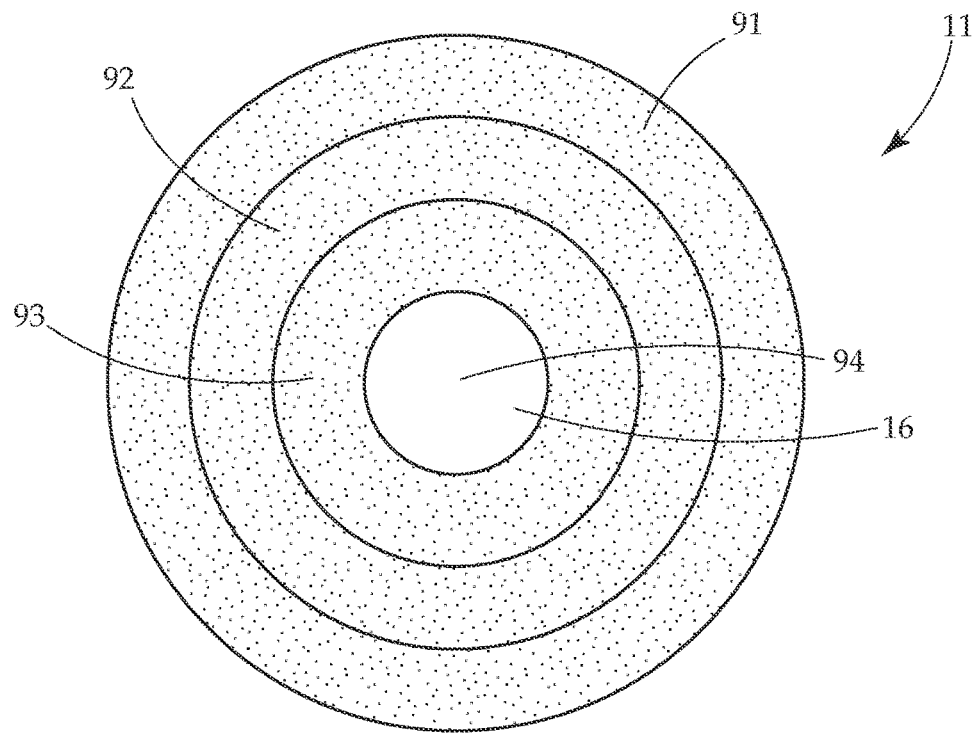
FIG. 9 provides a cross sectional view of one embodiment of the air purification system.

FIG. 9 provides a view of multiple different filter layers. In this view, a coarse filter layer 91 is on the outside, followed by a finer HEPA filter layer 92, and followed by a charcoal filter 93 to absorb odors and other chemical components. Interior space 94 lies at the center, and in operation the reflector and UV light source are positioned therein.

Figure 10:
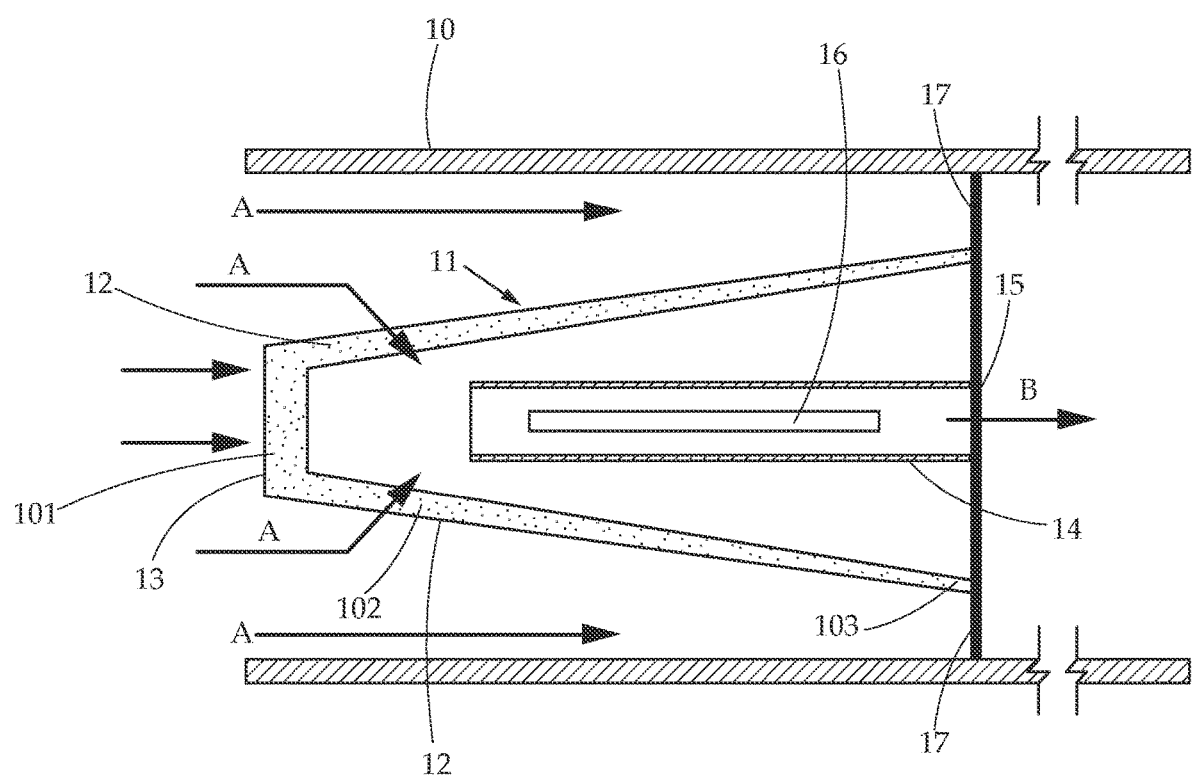
FIG. 10 provides a side view of still yet another embodiment of the air purification system positioned in an air duct.

Turning to FIG. 10 a side cutaway view of another embodiment of the air purification system is provided. The air purification system is positioned in a duct 10 allowing airflow A to pass through which exits the air purification system as purified flow B through outlet 15. The air purification system 11 has a filter 12 which has a thickness which tapers from a thick end to a thinner end. This thickness taper corresponds to regions within the duct 11 having higher or lower pressures. In this view, at the upstream end, filter 12 is thicker than at the downstream end because, in this configuration, there is more air upstream and as it gets drawn into and through the filter, there is less air pressure to pass through at the downstream end. A thinner filter at the downstream end allows adequate air flow through the filter, thereby increasing the overall area of the filter which can be used for filtration, and therefore allowing a greater air flow through the filter. The thickest portion is at the front face 101 facing the air flow. The side portion of the filter 12 at the upstream end has medium thickness 102 and this tapers down to the thinnest filter portion 103 at the downstream end. The air purification system 11 is sealed to the duct 10 at seals 17 to prevent air from passing over and around the filter 12, ensuring that all of air flow A goes through the filter 12. As will be understood, filter thickness taper may not be so drastic, and this is shown for display purposes. Depending on embodiment, tapering or other thickness reductions may be much more subtle. Other configurations to cause thickness of the filter to be thicker on one and thinner at another may be used. In this view, the filter 12 is shaped as a conical frustum with a conical frustum interior space.

Within the filter 12 is an interior space. Within the interior space, air is caused to flow through a reflector 14 which forms a channel and connects to outlet 15. Enclosed by the reflector is a UV light source 16 which emits UV-germicidal wavelengths to damage, destroy, deactivate and weaken pathogens and other biological materials. As noted above, the reflector 14 functions to both protect the filter material 12 from the UV light which will damage and degrade the material over time, and also serves to increase UV radiation exposure of the air passing through the reflector-defined channel. The reflector 14, in this embodiment, is positioned such that it extends past the ends of the UV source 16. This helps limit exposure of filter 12 to the UV light but preventing escape of nearly all of the UV light from UV source 16.

While several variations of the present disclosure have been illustrated by way of example in preferred or particular embodiments, it is apparent that further embodiments could be developed within the spirit and scope of the present disclosure, or the inventive concept thereof. However, it is to be expressly understood that such modifications and adaptations are within the spirit and scope of the present disclosure, and are inclusive, but not limited to the following appended claims as set forth.

What is claimed is:

1. An air purification system comprising:
   a filter formed into a cylinder or conical frustum shape, the filter defining an interior space;
   the filter formed of a filter material, wherein the filter material has a first thickness at a first end of the filter and second thickness at a second end of the filter, the first thickness being greater than the second thickness; and
   an ultraviolet light source positioned within the interior space, the ultraviolet light source configured to irradiate a quantity of air within the interior space, wherein the ultraviolet light source is at least partially surrounded by a reflector positioned within the interior space, the reflector operable to reflect ultraviolet light from the ultraviolet light source, and positioned to prevent exposure of the filter to the ultraviolet light from the ultraviolet light source.

2. The air purification system of claim 1 wherein the reflector is formed of aluminum.

3. The air purification system of claim 1 further comprising an air outlet at the second end of the filter downstream of an air flow of the ultraviolet light source.

4. The air purification system of claim 1 wherein the filter is pleated.

5. The air purification system of claim 1 wherein the filter further comprises a plurality of filter layers.

6. The air purification system of claim 5 wherein the plurality of filter layers comprises a coarse filter layer, a HEPA filter layer, and a charcoal filter layer.

7. The air purification system of claim 1 wherein the thickness of the filter tapers from the first end to the second end, and wherein the tapering thickness is configured to provide an approximately equal flow rate through the filter at the first end and second end.

8. The air purification system of claim 1 wherein the thickness of the filter tapers from the first end to the second end, and wherein the tapering thickness is configured to provide an approximately equal pressure within the interior space.

9. The air purification system of claim 1 wherein the first thickness on the thicker first side of the filter is on an upstream side of the filter relative to the second side of the filter.

10. The air purification system of claim 1 further comprising a conveyance system comprising a plurality of wheels, a motor, and a computer controller, the conveyance system allowing a controlled movement of the air purification system.

11. The air purification system of claim 10 further comprising an air quality sensor, the air quality sensor configured to provide an input to the computer controller, the computer controller programmed to control a movement of the air purification system independently or based on the input from the air quality sensor.

12. The air purification system of claim 10 wherein the motor is a universal motor.

13. The air purification system of claim 10 wherein the computer controller is operable to control an operation of at least one of the motor and conveyance system, the UV light source, and a fan, and wherein the computer controller is in communication with a remote computerized interface via a wireless or wired connection.

14. The air purification system of claim 1 wherein the filter and the reflector are electrically grounded by being electrically grounded, thereby reducing alpha and beta radiation passing through the air purification system.

15. The air purification system of claim 1 wherein the interior space is approximately cylindrical.

16. The air purification system of claim 1 is shaped approximately as a conical frustum.

17. The air purification system of claim 1 further comprising at least one of a humidifier and a dehumidifier positioned downstream on an air flow path of the ultraviolet light source.

18. The air purification system of claim 1 further comprising a humidifier positioned downstream on an air flow path of the ultraviolet light source, and further comprising a purified water inlet to the humidifier.

19. An air purification system positioned in an air duct comprising:
   a filter formed into a cylinder or conical frustum shape, the filter defining an interior space;
   the filter formed of a filter material, wherein the filter material has a first thickness at a first end of the filter and second thickness at a second end of the filter, the first thickness being greater than the second thickness;
   an ultraviolet light source positioned within the interior space, the ultraviolet light source configured to irradiate a quantity of air within the interior space, wherein the ultraviolet light source is at least partially surrounded by a reflector within the interior space, the reflector positioned to reflect ultraviolet light from the ultraviolet light source, and positioned to prevent exposure of the filter to the ultraviolet light from the ultraviolet light source; and
   a seal connecting the second downstream end of the filter to the air duct, the seal preventing air flow around the filter and causing air to pass through the filter.

20. The air purification system of claim 16 wherein a major axis of the air purification system is parallel to a major axis of the air duct.

21. The air purification system of claim 16 wherein the filter tapers in thickness being thickest at the first end and thinnest at the second end.

22. The air purification system of claim 18 wherein the first end is upstream in the air duct from the second end.

23. A method of operation of an air purification system in an air duct comprising the steps of:
   passing air through the air duct such that the air passes through a filter of the air purification system, the filter formed of a filter material, wherein the filter material has a first thickness at a first end of the filter and second thickness at a second end of the filter, the first thickness being greater than the second thickness;
   exposing air to ultraviolet light from an ultraviolet light source, the ultraviolet light source positioned within an interior space defined by the filter, and comprising a reflector positioned within the interior space between the ultraviolet light source and the filter to prevent degradation of the filter by ultraviolet light; and causing the filtered and ultraviolet-exposed air to exit the air purification system via an outlet.

\* \* \* \* \*